United States Patent [19]

Spotnitz et al.

[11] Patent Number: 4,692,227
[45] Date of Patent: Sep. 8, 1987

[54] OXIDATION OF ORGANIC COMPOUNDS USING THALLIUM IONS

[75] Inventors: Robert M. Spotnitz, Baltimore; Robert P. Kreh, Jessup, both of Md.

[73] Assignee: W. R. Grace & Co., New York, N.Y.

[21] Appl. No.: 936,521

[22] Filed: Dec. 1, 1986

[51] Int. Cl.$^4$ ................................. C25B 3/02
[52] U.S. Cl. ...................... 204/78; 204/72; 204/79; 204/80
[58] Field of Search .............. 204/78, 79, 80, 59 R, 204/72

[56] References Cited

U.S. PATENT DOCUMENTS

| | | | |
|---|---|---|---|
| 808,905 | 12/1905 | Lang | 204/78 |
| 3,048,636 | 8/1962 | Grinstead | 260/586 |
| 3,413,203 | 11/1968 | MacLean | 204/79 |
| 3,486,992 | 12/1969 | Frye | 204/86 |
| 3,641,067 | 2/1972 | Kruse | 260/348.52 |
| 3,873,580 | 3/1975 | Rennie | 260/362 |
| 4,031,196 | 6/1977 | Leonard | 423/624 |
| 4,135,051 | 1/1979 | Walker | 560/105 |
| 4,212,710 | 7/1980 | Halter et al. | 204/78 |
| 4,212,711 | 7/1980 | Halter et al. | 204/78 |
| 4,312,721 | 1/1982 | Oehr | 204/78 |
| 4,313,804 | 2/1982 | Oehr | 204/93 |
| 4,354,904 | 10/1982 | Malloy et al. | 204/59 R |
| 4,371,431 | 2/1983 | Switzer et al. | 204/78 |
| 4,387,007 | 6/1983 | Seiler | 204/59 R |
| 4,482,438 | 11/1984 | Ballard et al. | 204/78 |
| 4,530,745 | 7/1985 | Komatsu et al. | 204/130 |
| 4,536,337 | 8/1985 | Komatsu et al. | 260/396 R |
| 4,560,804 | 12/1985 | Yeh et al. | 568/408 |
| 4,582,942 | 4/1986 | Comninellis et al. | 568/426 |
| 4,639,298 | 1/1987 | Kreh et al. | 204/59 R |

FOREIGN PATENT DOCUMENTS

| | | |
|---|---|---|
| 899856 | 5/1972 | Canada . |
| 1132996 | 10/1982 | Canada . |

OTHER PUBLICATIONS

Australian Journal of Chemistry, 32, 737-753, (1979). J. Org. Chem., (1983), vol. 48, pp. 1487-1491 by M. Marrocco et al.
Prospects for the Indirect Electrolytic Oxidation of Organics by Ibl et al., Electro-Organic Synthesis Technology, No. 185, vol. 75, (1979), pp. 45-50.

Primary Examiner—Arthur P. Demers
Attorney, Agent, or Firm—Howard J. Troffkin

[57] ABSTRACT

Aqueous acidic solutions of certain thallium(III) organosulfonate having at least 0.1 molar thallium ion concentration are contacted with an organic compound to form a related oxidized organic compound. The oxidized compound is separated and recovered from the solution and the resultant thallium(I) rich solution is electrochemically treated to regenerate thallium(III) which, in turn, can be reused in a cyclical process.

The present invention provides a highly effective means of oxidizing organic substrates.

31 Claims, No Drawings

OXIDATION OF ORGANIC COMPOUNDS USING THALLIUM IONS

BACKGROUND OF THE INVENTION

The present invention is directed to an improved electrochemical process for oxidizing organic compounds and an effective means for regeneration of the spent oxidant. More specifically, the invention described and claimed herein requires the use of an organicsulfonic acid solution having certain thallium(III) organosulfonates dissolved therein as fully described hereinbelow.

The products achieved by the present invention have been previously formed to one degree or another by a variety of processes which can be classified as chemical or electrochemical. Various known oxidizing agents have been used to cause chemical oxidation of organic compounds. Oxidation has also been achieved by direct electrochemical oxidation, normally in the presence of an acidic electrolyte solution, as described in U.S. Pat. Nos. 4,298,438 and 4,354,904. Indirect electrochemical oxidation has been conducted in which the oxidant is electrochemically generated and then used to oxidize the organic substrate. Indirect electrolytic oxidation is discussed by Norbert Ibl et al at page 45 et seq. in Electro-organic Synthesis Technology, 75, No. 185 (1979) which teaching is incorporated herein by reference.

Compounds which are known to be capable of acting as an indirect oxidant include transition metal salts, particularly the metals of cobalt, chromium, manganese, iron, lead, silver and cerium. Because regeneration of the spent metal to its higher oxidation state is not always highly effective and/or other insoluble salts, such as oxides, etc., are formed, those skilled in this art tend to use the salts of chromium, manganese, cobalt, iron or lead as these salts are less expensive and replacement of spent materials do not greatly detract from the economics of the process. However, each of these metal ion oxidants have certain properties which cause them to make the oxidation process ineffective. For example, chromium ions give poor selectivity towards the desired products, cerium and manganese salts are believed to have low solubility of the oxidized and/or reduced ions in acidic solutions, the higher oxidation states of silver, cobalt and lead ions are not very stable and, in the case of iron, is not very reactive. Indirect electrochemical oxidation has been further complicated by the properties of the anion specie present. For example, certain anions (e.g., chloride, nitrate, perchlorate) are highly reactive with the organic substrate producing by-products or conditions which preclude their use on a commercial scale. Other less reactive anions (e.g., sulfate, acetate, fluoride, boron fluoride, silicon fluoride) generally form salts of low solubility, inhibit the rate of reaction of the oxidant with the organic substrate and/or inhibit the ability of the spent oxidant to be regenerated.

Thallium is a known oxidizing agent which has the potential of presenting an excellent two electron oxidant but has not been previously used to an extensive degree or on an industrial scale because of the inability of both the thallium(I) and thallium(III) species to be maintained in solution at high concentrations and due to the difficulty of generating the thallic oxidant in a simple and effective manner. For example, U.S. Pat. No. 3,048,636 teaches the use of low concentrations of thallium sulfate in order to avoid precipitation of either thallium(III) oxides, thallium(I) sulfate or complexes formed from thallium(I) and (III) sulfate. Thallium sulfates are generally restricted to low concentrations or must be used as a slurry. Both conditions are associated with poor reactivity and selectivity. One of the few thallium salts which exhibits high solubility is thallium(III) perchlorate. However, a potentially explosive situation is formed when the perchlorate anions are placed in contact with organic compounds.

The thallium salts are prohibitively expensive and must, therefore, be capable of being stable, react with the organic substrate cleanly and be easily regenerated to its higher valence state. This requires the thallium(III) salt to exhibit a high degree of stability and solubility in the reaction medium and be capable of achieving good reaction rates. In addition, the thallium(I) ion must also be highly soluble to be capable of being regenerated to the thallium(III) ion under conditions of high current efficiency at the anodic portion of the electrochemical cell. It has heretofore been believed that thallium must be used under a very narrow set of conditions or under inefficient conditions which could not demonstrate the potential necessary to provide an effective industrially suitable process.

Various processes are known to generate thallic ions from thallous ions but the majority of them are either expensive to do, require additional oxidant which precludes the systems use in providing a clean organic synthesis, causes accumulation of undesirable by-products, has a low efficiency of ability to generate the thallic ion or a combination of these defects. For example, chemical oxidation of thallous is, of course, possible with the very powerful agents such as chlorine gas and aqua regia, but these materials are objectionable as being somewhat difficult to handle (requiring expensive low-corrosion equipment), and cause the accumulation of undesirable materials in the system.

Hirose et al., in U.S. Pat. No. 3,399,956, report a system for oxidizing thallium with oxygen, which involves an acidic aqueous medium containing chloride or bromide and an ion of a "redox metal" such as copper or iron. In U.S. Pat. No. 3,479,262, MacLean et al describe a process to oxidize an olefin using thallium. The thallic ion is regenerated by a noble metal catalyzed oxidation using cerium(IV) as the oxidizing agent.

Other systems for oxidizing thallium are described in U.S. Pat. Nos. 3,486,992 to Frye, 3,759,804 to LeBris et al., 4,031,196 to Lenard, 4,115,420 to Brill, 4,115,421 to Brill, 4,058,592 to Rizkalla, 4,371,431 to Switzer et al as well as other methods.

Each of the above processes of forming thallium(III) has one or more disadvantage which makes it inappropriate for use in being an effective oxidant for organic compounds. In most instances either the thallous or the thallic specie is insoluble in the reaction medium. When the thallous specie is insoluble it impedes the separation and recovery of the organic product as well as lowering the effective oxidation to thallic ions. When the thallic specie is of low solubility, it reduces its effectiveness as an oxidant for the organic substrate.

It must be understood that although thallous/thallic ions have been known and used in oxidation reactions, there is a need to have a system wherein the thallic oxidant can be sufficiently stable under oxidizing conditions to be useful in indirect electrochemical processes, to be capable of undergoing repeated cycling between its thallous ($Tl^{+1}$) and thallic ($Tl^{+3}$) species in a high degree of efficiency under the reaction and electrolysis conditions, to be capable of exhibiting high reaction rates to make the process attractive on a commercial scale, to have high solubility to aid in the efficiency of the reaction and to eliminate the problems associated with slurries of thallium salts. It is readily seen that a means of achieving this combination of desired properties would aid in providing a process which would find a high degree of acceptance in electrochemical oxidation of organic compounds.

SUMMARY OF THE INVENTION

The present invention is directed to an electrochemical process wherein thallium(III) ions are generated and used as an oxidant to transform organic compounds to their corresponding carbonyl and/or hydroxyl containing compounds. The present process requires the utilization of at least 0.1 molar concentration of thallium salts of certain organosulfonic acids dissolved in an acidic solution containing an excess of the corresponding free organosulfonic acid. The acidic thallium salt solution, as described hereinbelow, exhibits the desired combination of properties (stability, solubility, reactivity, capability to achieve high current density, and capability of repeated cycling between thallous and thallic species) to provide a commercially attractive process.

DETAILED DESCRIPTION OF THE INVENTION

The present invention provides an improved indirect electrochemical oxidation process. The improvement requires the utilization of thallium salts of certain organosulfonic acids present in concentration of at least 0.1 molarity in aqueous solution containing the corresponding free acid in at least about 1 Normality to provide efficient reaction rates for oxidizing the organic substrate and high current efficiency to regenerate the oxidant.

The term "organosulfonic acid" and "organosulfonates" as used herein and in the appended claims shall refer to the free acid and salts of the free acid, respectively, wherein the acid has the general formula

RSO$_3$H in which R represents methyl, trifluoromethyl, benzyl or tolyl group. The subject term shall include each individual acid or mixtures thereof. The preferred organosulfonic acid is methanesulfonic acid.

As discussed above, certain salts have anions which have detrimental effects on the system or the salt, in either its oxidized or reduced form or in combination, or has low solubility in acid solutions. For example, thallium sulfate is known to have limited solubility in weakly acidic solutions. Similarly, the acetate and oxide salts have low solubility in such solutions. Although nitrate and perchlorate salts are soluble, they are not suitable for industrial processes due to the degree of reaction they have with the organic substrate.

It has now been unexpectedly found that the subject thallium organosulfonates can be used as effective oxidants for indirect electrochemical synthesis when used according to the present invention which requires the solution to contain an excess of organosulfonic acid corresponding to salt used. The excess should preferably be at least about 1 and most preferably from 1 to about 9 Normal free acid (with respect to thallous) in the solution, to have the thallium salts substantially completely dissolved in the solution and to have the combined thallium ion concentration be at least 0.1 molar. The utilization of the presently required solution unexpectedly provides the combination of advantages of:

(1) high solubility of both the thallous and the thallic ions over a wide acid concentration;

(2) high current efficiency at high current density (of at least about 75 mA/cm$^2$ or greater) to provide effective anodic oxidation of the thallous ions to thallic ions;

(3) fast reaction rate of the thallic oxidant with the organic reactant;

(4) passivity of the anion and the free acid to the organic reactant and to the electrodes of the cell; and (5) clean, uncomplicated reduction at the cathode to again aid in effecting an efficient process.

The subject process requires the use of the salts of thallium organosulfonate, most preferably thallium methanesulfonate. Solutions of the salts can be readily formed by reacting a thallium salt of an inorganic acid with aqueous solution of the organosulfonic acid. The resulting aqueous solution should, preferably, be substantially free of extraneous anions of other acids such as sulfates, nitrate, perchlorate, halide, acetate, trifluoroacetate and the like. It is preferred that the concentration of such extraneous anions be maintained at a low value of from 0 to 0.5 preferably from 0 to 0.1 mole per mole of thallium ions present in the solution. It is therefore most desired to form the subject salts from thallous carbonate, thallous hydroxide, thallous oxide and the like and most preferably from the carbonate. When other inorganic acid salts are used, their anions should be substantially removed from the solution by known means prior to using solution in the subject process. For example, if sulfate ions are present they can be removed by precipitation with lead(II) carbonate. Similarly, chloride ions can be removed by treating the solution with silver carbonate. Other extraneous ions can be removed in similar manners known in the art.

As discussed above, various thallium salts have been proposed as an oxidant in electrochemical oxidation processes. The salts have been either formed from reactive anions or from a more passive anion in which case the salt is normally present in the form of a slurry due to solubility restrictions attributable to salts of either one or both of the metal ions (e.g. Tl$^{+1}$,Tl$^{+3}$). The present invention unexpectedly provides a means of maintaining high concentrations of both the thallic and thallous species in solution and thus permits cyclical formation of the ions without formation of insoluble material. The present process requires the electrolytic solution to contain certain free organosulfonic acids in at least 0.1 molar concentration, normally from 1 to 9 molar and preferably from 1.5 to 8 molar concentration. Further, it is preferable that the electrolytic solution be substantially free of inorganic acids although small amounts may be present.

The solution in which the process of the present invention is conducted can be an aqueous solution containing the above described concentrations of thallium organosulfonate and of the corresponding free organosulfonic acid. Alternately, the subject process of transforming the thallous ions to thallic ions and using the latter as an oxidant for an organic substrate can be conducted in solutions formed with an organic polar liquid. The organic polar compound should be liquid under the reaction process conditions and should be substantially inert with respect to oxidation by the thallic ion present and substantially inert with respect to the organic substrate. These properties can be readily determined by simple tests. Suitable liquids include compounds containing one or more groups selected from nitriles, alcohols, amides, ethers, and nitro groups and mixtures thereof. In addition, the process can be carried out in an alkane sulfonic acid. Examples of suitable nitriles include alkyl nitriles wherein the alkyl is a $C_1$-$C_{10}$, preferably a $C_1$-$C_5$ alkyl group such as acetonitrile propionitrile, butyronitrile and the like. Examples of suitable hydroxyl containing compounds include $C_1$-$C_{12}$ alkyl alcohols such as methanol ethanol, butanol, dodecanol, ethylene glycol and the like. Examples of suitable amides include alkylamides such as N,N-dimethylformamide pyrrolidone and the like. Examples of suitable ethers include dialkyl ethers, polyethers and alkyl, aryl ethers such as ethyl ether, methyl ethyl ether, phenyl ether, ethyl phenyl ether, diglyme and the like. The nitro compounds which are suitable include nitroparafins such as nitromethane, nitroethane, 1-nitropropane, 2-nitropropane and the like. The above described polar organic liquids can be used in combination with water or can be used separately as the reaction medium.

The process can also be carried out neat in an alkyl sulfonic acid such as with only excess methanesulfonic acid or the like.

The thallic and thallous salts can be dissolved in the presently described solution at high concentrations without causing precipitation of either one of the salt species. The solution can have a combined concentration of thallic and thallous metal ions at levels of 0.1 molar or greater under the process temperature conditions. Thallium concentrations of 0.5 molar and greater can be readily achieved. It is realized that under the present process, the thallium ions can be maintained in solution at concentrations which are higher or less than the above stated concentrations provided they are maintained in solution. The specific concentration which meet economic process and solubility restraints can be readily determined by conventional techniques.

Organic compounds which can be reacted with thallium(III) include those which have an index of hydrogen deficiency greater than zero. This index is described by J. B. Hendrickson, D. J. Cram and G. S. Hammond, Organic Chemistry, Third Edition, McGraw-Hill, Inc., 1970, at pages 72-73 and 82-83, as the number of pairs of hydrogen atoms which must be removed from a saturated alkane to give the empirical formula of a subject compound. For a hydrocarbon, then, the index represents the total of the rings and multiple bonds in a molecule. For compounds containing heteroatoms, the following principles can be used to make the index application: (1) oxygen and sulfur atoms do not change the index; (2) each halogen atom is equivalent to one-half of a hydrogen atom pair; and (3) each nitrogen atom requires that the "reference" saturated alkane be considered as having one extra hydrogen atom (i.e., a formula of $C_nH_{2n+3}$).

It is known that olefins can be oxidized with thallium to form carbonyl compounds and glycols (Grinstead, J. Org. Chem. Vol. 26, Pg. 238–240, 1961; and P. M. Henry, Homogeneous Catalysis, ACS Advances in Chemistry Series, Vol. 70, Pg. 126-154, 1968). Ethylene is oxidized to ethylene glycol and acetaldehyde. Kruse and Bednarski have reported in J. Org. Chem. Vol. 36, Pg. 1154-1155 (1971) that the oxidation can be stopped under certain conditions to provide the corresponding epoxide. For example, under weakly solvating conditions, propylene forms propylene oxide in good yields.

In addition to the oxidation of olefins, many other organic reactions occur with thallium. A review by R. J. Quellette, "Oxidation by Thallium(III)," Chapter 3 of Oxidation in Organic Chemistry, Part B, W. S. Trahanovsky, Ed., Academic Press, 1973, discusses work which has been done in the oxidation of steroids, oxidative rearrangement of chalcones, oxidative cleavage of cycloalkanes, oxidation of carbonyl compounds, oxidation of phenols, and the conversion of benzene to phenol.

Each of the above cited teachings of Hendrickson et al., Grinstead, Henry, Kruse et al. and Quellette are incorporated herein by reference.

The aqueous solution may contain an organic co-solvent which can aid in solvating the organic reactant. The co-solvent may be miscible or immiscible with the aqueous phase. Such co-solvents may be any which is inert in the system and can be selected from the classes of polar organic liquids discussed above. Other conventional materials may be added to the system provided they are inert to the thallium salt and free acid used herein. Examples of such materials include anionic surfactants such as sodium dodecylbenzene sulfonate and the like and cationic surfactants such as tetrabutylammonium hydroxide and the like.

The generation and subsequent regeneration of thallic oxidant can be readily carried out by supplying the solution of the present invention to an electrolytic cell in either a batch or continuous manner. The cell is preferably divided into catholyte and anolyte sections by a porous partition wall or membrane. The membrane should be selected from membranes capable of permitting hydrogen proton transfer. The electrodes may be of any suitable form such as plates, lattices, expanded metal, or reticulated porous material and the like. The anode may be any of the known materials suitable for preforming the metal-ion oxidation and are, preferably selected from lead, lead oxide, platinum, platinized titanium, platinized niobium or metal oxide-titanium composite. The cathode of the cell may be any of the known materials suitable for performing reductions in the aqueous-acid solutions with or without the presence of metal ions such as, for example, steel, copper, and nickel. The use of the presently described thallium salt solution has, as one of its unexpected properties, the ability to readily and effectively generate and regenerate thallic oxidant from thallous ions at high current density. Another unexpected property is the ability of the solution to cause a clean cathodic reduction without production of by-products which detract from the process and require separation therefrom. The electrolysis can be performed at voltages ranging from about 1.5 to 20 volts with current density ranging between about 0.1 to about 500 mA/cm$^2$, preferably from 10 to 400 mA/cm$^2$ and most preferably from 30 to 300 mA/cm$^2$ (based on electrode area excluding roughness factor). The electrolysis may be conducted at a temperature of from about $-20°$ to 150° C. and preferably from 0° to 100° C. It is most preferable to have the cell temperature and the reaction temperature (where the cell and chemical reactor are separate) be substantially the same.

The organic compounds described above are oxidized by contacting the organic compound with the acidic aqueous solution described above which contains the subject oxidant, thallic organosulfonate. The contacting of the oxidant and the organic compound may be conducted directly within the electrolytic cell. However, it is preferable to transfer the subject oxidant containing solution to a separate reactor vessel where it is contacted with the organic compound to be oxidized under agitation. The organic compound can be introduced to the reactor either dissolved or dispersed in the aqueous phase or dissolved in a co-solvent with the aqueous solution.

It has been unexpectedly found that the solution used in the present process is capable of providing thallic ions in high concentration and at high solubility in the liquid phase to provide high reaction rate in oxidizing the organic compound. The organic oxidation can be carried out under ambient temperature and pressure conditions. The temperature may be varied from about 0° to about 100° C. with from 20° to 75° C. being preferred. The pressure may be elevated or reduced for process reasons.

The solution removed from the reaction zone contains product and spent metal ion oxidant (thallous). The product can be readily separated from the solution by phase-separation, distillation, precipitation or extraction with an appropriate solvent such as dichloroalkanes, cyclohexane and the like. The particular mode of separation will depend upon the identity of the product formed and can be readily ascertained by the artisan.

The resultant solution (after separation of the product) will contain thallous salt as the sole or major component and may contain small amounts of unreacted thallic salt. This solution can be returned to the electrolytic cell for regeneration of the thallic ion oxidant. It has been found that the thallic/thallous salts used herein readily regenerate a multiplicity of cycles without formation of by-products which have detrimental effect on the efficiency of the process.

The following examples are given for illustrative purposes only and are not meant to be a limitation on the present invention as defined by the claims appended hereto. All parts and percentages are by weight unless otherwise indicated.

EXAMPLE I 35 parts of an aqueous solution containing 0.5 molar concentration of thallous methanesulfonate and 63.5 Normal concentration of methanesulfonic acid was electrolyzed in a divided cell using platinum electrodes. After passage of 0.015 Faradays the solution remained clear and a corresponding amount of thallium was oxidized to Tl(III).

EXAMPLE II 35 parts of an aqueous solution containing 0.5 molar concentration of thallous sulfate and 3.5 Normal concentration of sulfuric acid was electrolyzed in a divided cell using platinum electrodes. After passage of 0.0041 Faradays the solution became cloudy and a precipitate formed.

EXAMPLE III 25 parts by volume of an aqueous solution having 0.24 molar thallic methanesulfonate and 2 molar free methanesulfonic acid was stirred while adding 0.416 parts of chalcone (benzylidene acetophenone) in 15 parts of 1,2-dimethoxyethane. The solution was heated to 85° C. and maintained at the temperature with stirring for 18 hours. The resulting solution was extracted with 1,2-dichloroethane and then analyzed by gas chromatography. The results showed an 84% conversion of the chalcone and about 20 percent selectivity to benzil (diphenylglyoxal).

We claim:

1. A process for oxidizing organic compounds comprising contacting an organic compound having an index of hydrogen deficiency greater than zero with a solution containing thallic organosulfonate salt in the presence of an excess of the corresponding free organosulfonic acid, said organosulfonic acid having the general formula $RSO_3H$ wherein R represents methyl, trifluoromethyl, benzyl, tolyl and mitures thereof and said solution being substantially free of extraneous anions of inorganic acids and having at least 0.1 molar thallium concentration; and separating and recovering the oxidized product from the solution to yield a spent solution rich in thallous salts.

2. The process of claim 1 wherein the free acid concentration is from 0.1 to 9 molar and the thallium organosulfonate salts are dissolved in said solution.

3. The process of claim 1 wherein said solution is an aqueous solution.

4. The process of claim 2 wherein said solution is an aqueous solution.

5. The process of claim 3 wherein R represents methyl.

6. The process of claim 4 wherein R represents methyl.

7. The process of claim 5 wherein the solution has a concentration of extraneous anions of from 0 to about 0.5 mole per mole of thallium ions present.

8. The process of claim 5 wherein the organic compound and thallic salt solution are contacted at a temperature ranging from 0° to 100° C.

9. The process of claim 6 wherein the organic compound and thallic salt solution are contacted at a temperature ranging from 0° to 100° C.

10. The process of claim 5 wherein the aqueous solution further contains an organic solvent for the organic substrate, said organic solvent being miscible in the aqueous solution.

11. The process of claim 6 wherein the aqueous solution further contains an organic solvent for the organic substrate, said organic solvent being miscible in the aqueous solution.

12. The process for oxidizing organic compounds comprising contacting an organic compound having an index of hydrogen deficiency greater than zero with a solution containing thallic organosulfonate and excess of the corresponding free organosulfonic acid in an organic polar solvent, said organosulfonic acid having the general formula $RSO_3H$ wherein R represents methyl, trifluoromethyl, benzyl, tolyl and mixtures thereof and said solvent being substantially free of extraneous anions of inorganic acids and having at least 0.1 molar thallium concentration; and separating and recovering the oxidized product from the solution to yield a spent solution rich in thallous salts.

13. The process of claim 1 wherein the free acid concentration is from 0.1 to 9 molar and the thallium organosulfonate salts are dissolved in said solution.

14. The process of claim 12 wherein said solution is an aqueous solution.

15. The process of claim 13 wherein said solution is an aqueous solution.

16. The process of claim 14 wherein R represents methyl.

17. The process of claim 15 wherein R represents methyl.

18. The process of claim 16 wherein the solution has a concentration of extraneous anions of from 0 to about 0.5 mole per mole of thallium ions present.

19. The process of claim 16 wherein the organic compound and thallic salt solution are contacted at a temperature ranging from 0° to 100° C.

20. The process of claim 17 wherein the organic compound and thallic salt solution are contacted at a temperature ranging from 0° to 100° C.

21. The process of claim 16 wherein the aqueous solution further contains an organic solvent for the organic substrate, said organic solvent being miscible in the aqueous solution.

22. The process of claim 17 wherein the aqueous solution further contains an organic solvent for the organic substrate, said organic solvent being miscible in the aqueous solution.

23. The process of claim 1 wherein the solution is excess organosulfonic acid.

24. The process of claim 23 wherein R represents methyl.

25. An indirect electrochemical oxidation process to oxidize organic compounds comprising
  (a) contacting an organic compound having an index of hydrogen deficiency greater than zero with a solution containing thallic organosulfonate and having an excess of the corresponding free organosulfonic acid therein, said organosulfonic acid having the general formula $RS_3H$ wherein R represents methyl, trifluoromethyl, benzyl, tolyl and mixtures thereof and said solution having substantially all thallic and thallous ions dissolved in said solution and at a concentration of at least 0.1 molar;
  (b) separating and recovering the oxidized product from the solution to yield a spent solution rich in thallous salts;
  (c) transferring the spent solution to an electrochemical cell to cause regeneration of a solution rich in the thallic salt; and
  (d) repeating steps (a), (b) and (c).

26. The process of claim 25 wherein the solution comprises an aqueous solution having at least 1 molar concentration of free methanesulfonic acid therein and wherein R represents methyl.

27. The process of claim 25 wherein the solution comprises an organic polar liquid having at least 1 molar concentration of free methanesulfonic acid therein and wherein R represents methyl.

28. The process of claim 26 wherein the organic compound is introduced as a solution in an organic solvent.

29. The process of claim 26 wherein the aqueous solution contains a surfactant.

30. The process of claim 26 wherein the oxidation of the organic compound is performed in the electrochemical cell.

31. The process of claim 25 wherein said electrochemical cell is composed of anolyte and catholyte sections separated by a proton permeable membrane.

* * * * *